United States Patent [19]

Curran et al.

[11] Patent Number: 4,808,579

[45] Date of Patent: Feb. 28, 1989

[54] NOVEL MONOCYCLE β-LACTAM ANTIBACTERIALS

[75] Inventors: William V. Curran, Pearl River, N.Y.; Robert H. Lenhard, Paramus, N.J.

[73] Assignee: American Cyanamid Company, Stamford, Conn.

[21] Appl. No.: 120,282

[22] Filed: Nov. 13, 1987

[51] Int. Cl.$^4$ .................. C07D 417/12; A61K 31/425
[52] U.S. Cl. ...................................... 514/210; 540/363
[58] Field of Search ......................... 540/363; 514/210

[56] References Cited

U.S. PATENT DOCUMENTS 4,723,002 2/1988 Bisacchi ............................. 540/363

Primary Examiner—Mark L. Berch
Attorney, Agent, or Firm—Edward A. Conroy, Jr.

[57] ABSTRACT

The disclosure describes (S)-3-[2-(2-amino-4-thiazolyl)]-(Z)-2-methoxyiminoacetylamino-2-oxo-1-azetidinyliminoacetic acid and (S)-3-[2-(2-amino-4-thiazolyl)]-(Z)-2-methoxyiminoacetylamino-2-(S)-methyl-4-oxo-1-azetidinyliminoacetic acid and the cationic salts thereof which possess antibacterial activity.

5 Claims, No Drawings

NOVEL MONOCYCLE β-LACTAM ANTIBACTERIALS

SUMMARY OF THE INVENTION

The present invention relates to new organic compounds and more particularly is concerned with novel monobactam (monocyclic β-lactam) compounds that possess antibacterial activity, which may be represented by the following structural formula:

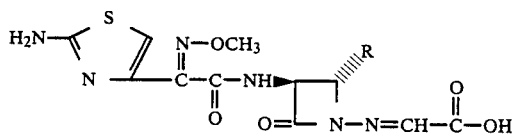

wherein R may be hydrogen or methyl and the pharmacologically acceptable salt cations thereof.

DETAILED DESCRIPTION OF THE INVENTION

Representative compounds of the present invention are appreciably soluble in solvents such as acetone, ethanol, toluene, methylene chloride and the like and are soluble in dilute aqueous sodium bicarbonate and may form a pharmacologically acceptable salt cation with an alkali metal such as sodium or potassium and the like.

The invention also relates to the synthesis of new compounds that possess antibacterial activity. More specifically, it relates to the synthesis of the novel monocyclic β-lactams as illustrated in Schemes 1 and 2.

Compound 12b in Scheme 1 and Compound 12a in Scheme 2 have been shown to exhibit antibacterial activity against various pathogenic bacteria in vitro.

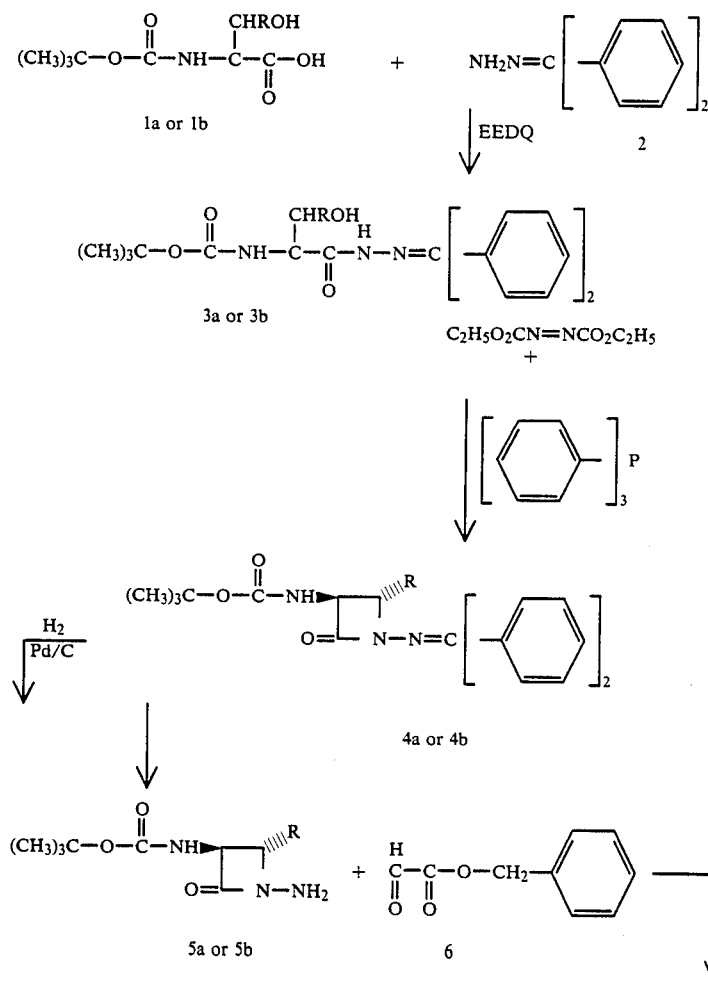

Scheme 1

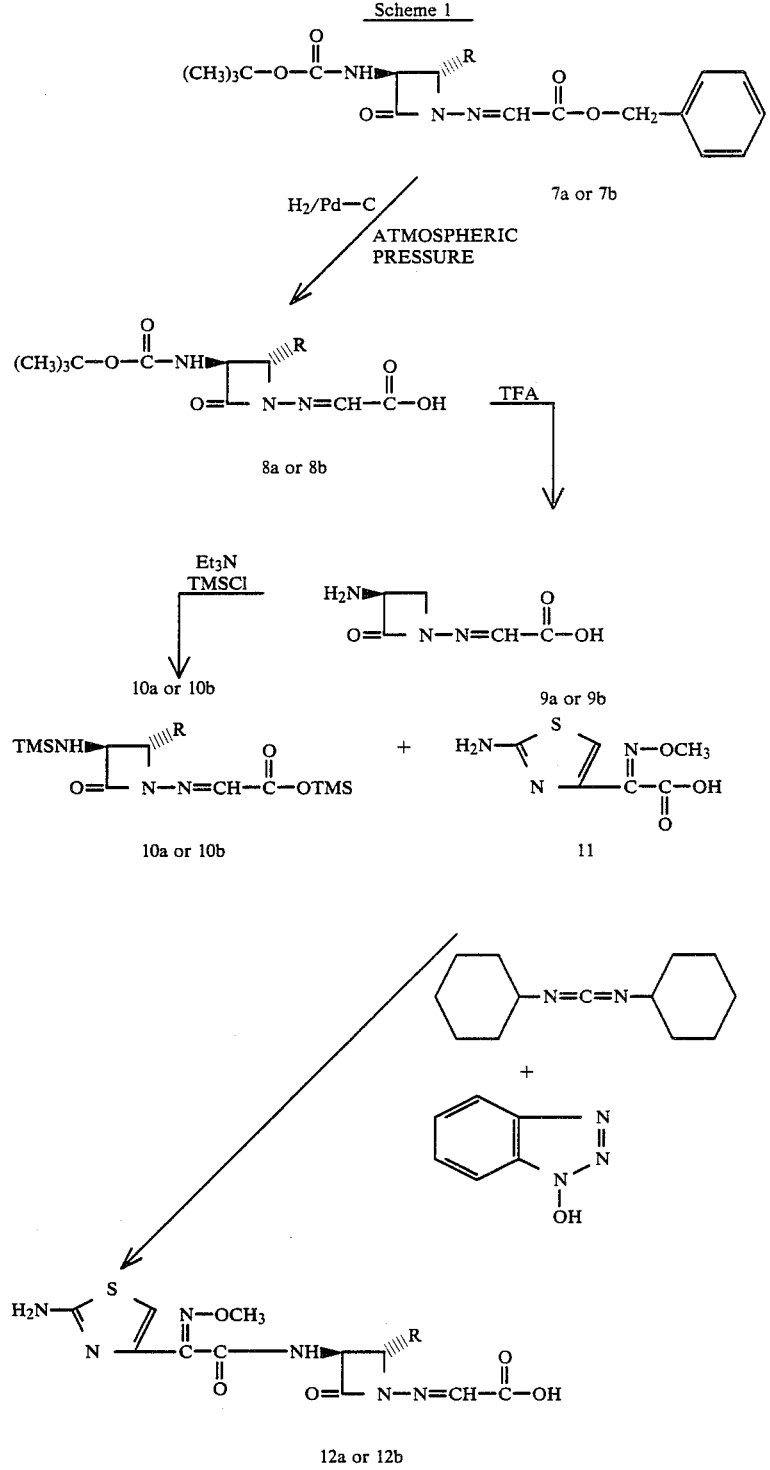

(a) R = H
(b) R = METHYL

In accordance with Scheme 1, the reaction of t-butyloxycarbonyl-L-serine (1a) with benzophenone hydrazone (2) in the presence of 2-ethoxy-1-(2H)-quinolinecarboxylic acid ethyl ester afforded the hydrazide derivative N-(t-butyloxycarbonyl)-L-serine-2-(diphenylmethylene)hydrazide (3a) which readily underwent ring-closure under Mitsunobo conditions using diethyl azodicarboxylate and triphenylphosphine to give the β-lactam t-butyl (S)-[1-[(diphenylmethylene)amino]-2-oxo-3-azetidinyl]-carbamate (4a) in good yield. Catalytic hydrogenation in a Parr apparatus produced the N-amino compound t-butyl (S)-1-amino-2-oxo-3-azetidinylcarbamate (5a). Reaction of compound (5a) with benzyl glyoxylate (6) afforded the imino derivative benzyl (S)-3-[t-butyloxycarbonylamino]-2-oxo-1-azetidinyliminoacetate (7a) which was converted to the amino derivative 3-(t-butoxycarbonylamino)-2-oxo-1-azetidinyliminoacetic acid (8a) by catalytic reduction in the presence of palladium on carbon at atmospheric pressure. Treatment of (8a) with trifluoroacetic acid afforded the aminoacid (S)-[(3-amino-2-oxo-1-azetidinyl)imino]acetic acid trifluoroacetate (9a). Condensation of the trimethylsilyl derivative (10a) with the activated ester of 2-(2-amino-4-thiazolyl)-2-methoxyiminoacetic acid (11) prepared from 1-hydroxybenzotriazole and N,N'-dicyclohexylcarbodiimide gave the desired monobactam derivative (S)-3-[[(2-amino-4-thiazolyl)(methoxyimino)acetyl]amino]-2-oxo-1-azetidinyliminoacetic acid 12a.

Also in accordance with Scheme 1 and starting with the reaction of t-butyloxycarbonyl-L-threonine (1b) with benzophenone hydrazone (2) in the presence of 2-ethoxy-1(2H)-quinolinecarboxylic acid ethyl ester the hydrazide derivative N-(t-butyloxycarbonyl)-L-threonine-2-(2-diphenylmethylene)hydrazide (3b) was obtained. Ring closure of (3b) as described above with diethyl azodicarboxylate and triphenylphosphine gave the β-lactam, t-butyl (S)-[1-[(diphenylmethylene)amino]-2-(S)-methyl-4-oxo-3-azetidinyl)-carbamate (4b). Catalytic hydrogenation of (4b) gave the N-amino compound t-butyl 1-amino-2-(S)-methyl-4-oxo-3-(S)-azetidinylcarbamate (5b) which was reacted with benzyl glyoxylate (6) to give the imino derivative benzyl [[4(S)-methyl-3(S)-[(t-butoxycarbonyl)amino]-2-oxo]imino]acetate (7b). Catalytic reduction of (7b) gave the amino derivative 4(S)-methyl-[[3(S)-[[(t-butyloxycarbonyl]amino]-2-oxo-1-azetidinyl]imino]acetic acid (8b) which was treated with trifluoroacetic acid to give the amino acid, [[(S)-3-amino-4-oxo-2-(S)-methyl-1-azetidinyl]iminoacetic acid trifluoroacetate (9b). Then condensation of the trimethylsilyl derivative (10b) with the activated ester of 2-(2-amino-4-thiazolyl)-2-methoxyiminoacetic acid (11) gave the desired monobactam derivative (S)-3-[2-(2-amino-4-thiazolyl)]-(Z)-2-methoxyiminoacetylamino-2-(S)-methyl-4-oxo-1-azetidinyliminoacetic acid (12b).

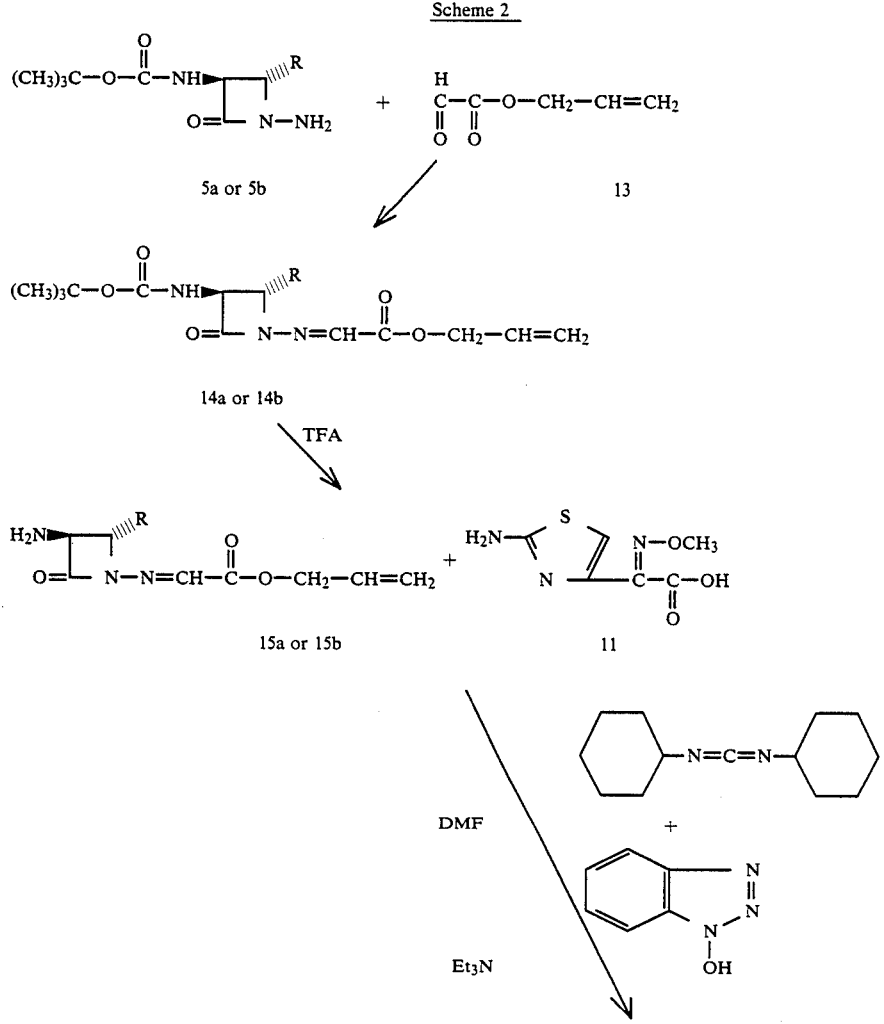

Scheme 2

-continued

Scheme 2

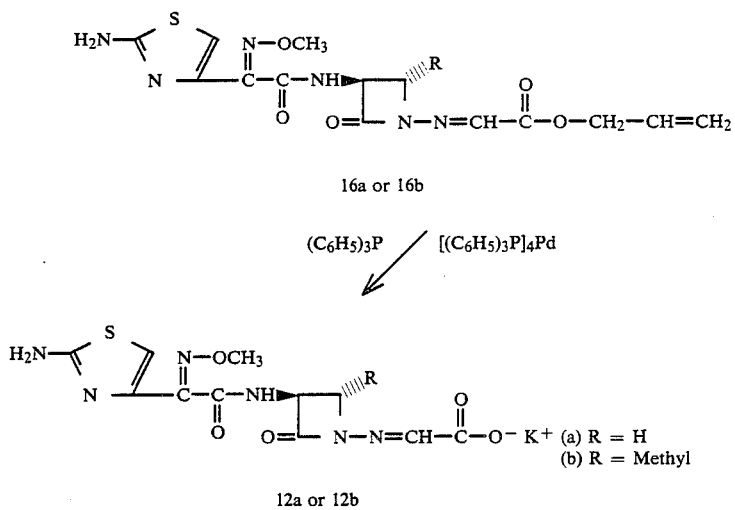

(a) R = H
(b) R = Methyl

In accordance with Scheme 2, the reaction of t-butyl (S)-1-amino-2-oxo-3-azetidinylcarbamate (5a) with allyl glyoxylate (13) afforded the imino derivative allyl (S)-3-[t-butyloxycarbonylamino]-2-oxo-1-acetidinyliminoacetate (14a). Treatment of (14a) with trifluoroacetic acid afforded the aminoacid, allyl(S)-[(3-amino-2-oxo-1-azetidinyl)imino]acetate trifluoroacetate (15a). Condensation of the aminoacid (15a) with the activated ester of 2-(2-amino-4-thiazolyl)-2-methoxyiminoacetic acid (11), (prepared as hereinbefore described), in the presence of dicyclohexylcarbodiimide, 1-hydroxybenzotriazole and triethylamine gave the compound allyl (S)-3-[(2-amino-4-thiazolyl)-(Z)-2-methoxyiminoacetylamino]-2-oxo-1-azetidinyliminoacetate (16a). Then treatment of (16a) with tetrakis(triphenylphosphine)palladium (O), triphenylphosphine and potassium 2-ethylhexanoate gave the desired monobactam derivative potassium S-[[3-[[(2-amino-4-thiazolyl)-(Z)-(methoxyimino)acetyl]amino]-2-oxo-1-azetidinyl]imino]acetate (12a).

The in vitro antibacterial activity of representative monobactam derivatives of the present invention was determined against a spectrum of gram-negative bacteria by a standard agar dilution method. Mueller-Hinton agar containing two-fold decreasing concentrations of the compound was poured into Petri plates. The agar surfaces were inoculated with 1 to $5 \times 10^4$ colony forming units of bacteria by means of a Steers replicating device. The lowest concentration of the monobactam derivative that inhibited growth of a bacterial strain after 18 hours of incubation at 35° C. was recorded as the minimal inhibitory concentration (MIC) for that strain. The results are summarized in Table I.

TABLE I

In Vitro Antibacterial Activity of Potassium (S)—[[3-[[2-Amino-4-Thiazolyl-(Z)—(Methoxyimino)Acetyl]Amino]-2-Oxo-1-Azetidinyl]imino]acetate (12a) and (S)—3-[2-(2-Amino-4-Thiazolyl)]-(Z)—2-Methoxyiminoacetyl-amino-2-(S)—Methyl-4-Oxo-1-Azetidinyliminoacetic Acid (12b)

| ORGANISM | | | MINIMAL INHIBITORY CONCENTRATION mcg/ml | |
|---|---|---|---|---|
| | | | (12a) | (12b) |
| Escherichia coli | MOR | 84-20 | 8 | 2 |
| Escherichia coli | VGH | 84-19 | 8 | 2 |
| Escherichia coli | CMC | 84-50 | 4 | 2 |
| Escherichia coli | ATCC | 25922 | 8 | 8 |
| Klebsiella pneumoniae | CMC | 84-31 | 8 | 2 |
| Klebsiella pneumoniae | MOR | 84-24 | 16 | 8 |
| Klebsiella pneumoniae | IO | 83-5 | 8 | 4 |
| Enterobacter cloacae | VGH | 84-39 | 16 | 8 |
| Enterobacter cloacae | K | 84-10 | 8 | 4 |
| Enterobacter cloacae | MOR | 84-30 | 64 | 32 |
| Serratia marcescens | MOR | 84-41 | 32 | 4 |
| Serratia marcescens | CMC | 83-74 | >128 | 16 |
| Serratia marcescens | IO | 83-63 | 32 | 8 |
| Morganella morganii | VGH | 84-12 | 64 | 4 |
| Morganella morganii | CMC | 84-38 | 32 | 8 |
| Morganella morganii | MOR | 84-45 | 128 | 16 |
| Proteus rettgeri | IO | 83-21 | 0.5 | 0.12 |
| Providencia stuartii | CMC | 83-3 | 32 | 2 |
| Citrobacter diversus | K | 82-24 | 16 | 4 |

The compounds of the present invention have been found to be highly useful as antibacterial agents in mammals, when administered in amounts ranging from about one milligram to about 250 mg per kilogram of body weight per day. A preferred dosage regimen for optimum results would be from about 5 mg to about 100 mg per kilogram of body weight per day, and such dosage units are employed that a total of from about 0.35 g to about 7.0 grams of the active ingredient for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation.

The active compounds of the present invention may be orally administered, for example, with an inert diluent or with an assimilable edible carrier, or they may be enclosed in hard or soft shell gelatin capsules, or they may be compressed into tablets, or they may be incorporated with excipients and used in the form of tablets, troches, capsules, elixiers, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active ingredient in such therapeutically useful compositions is such that a suitable dosage will be obtained. Preferred compositions or preparations according to the present invention are prepared so that an oral dosage unit form contains between about 25 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

This invention will be described in greater detail in conjunction with the following examples.

EXAMPLE 1

N-(t-Butyloxycarbonyl)-L-serine-2-(diphenylmethylene)hydrazide; (3a)

A solution of 20.0 g (0.10 mole) of t-butyloxycarbonyl-L-serine, 19.6 g (0.10 mole) of benzophenone hydrazone, and 24.7 g of 2-ethoxy-1(2H)-quinolinecarboxylic acid ethyl ester in 250 ml of methylene chloride was stirred at room temperature for 16 hours. The solution was extracted with successive 100 ml portions of 1N hydrochloric acid, water, saturated sodium bicarbonate solution, water and brine, then dried over magnesium sulfate. The solvent was evaporated in vacuo and the resulting syrup was dissolved in ethyl acetate and crystallized by the addition of hexane to afford 24.5 g (64%) of product, mp 150.0°–152.5° C.

EXAMPLE 2

N-(t-Butyloxycarbonyl)-L-threonine-2-(2-diphenylmethylene)hydrazide; (3b)

The procedure of Example 1 was followed using N-(t-butoxycarbonyl)-L-serine to obtain the desired product, mp 123°–126° C.; IR (KBr) 1680 and 1715 cm$^{-1}$ (—C=O).

EXAMPLE 3 t-Butyl (S)-[1-[(diphenylmethylene)amino]-2-oxo-3-azetidinyl]-carbamate; (4a)

A solution of 7.9 ml (0.05 mol) of diethyl azidodicarboxylate in 50 ml of tetrahydrofuran was added to a stirred solution of 9.6 g, (0.05 mol) of N-(t-butyloxycarbonyl)-L-serine-2-(diphenylmethylene)hydrazide and 9.6 g, (0.05 mol) of triphenylphosphine in 250 ml of tetrahydrofuran. The mixture was stirred and heated at 55° C. for 6 hours. The resulting solution was evaporated to dryness in vacuo. The residue was dissolved in 50 ml of ethyl acetate and chilled. The crystalline precipitate was removed by filtration and the filtrate was evaporated to dryness. The residue was chromatographed on silica gel using ethyl acetate-hexane (1:1) as the eluent to afford 12.0 g (66%) of the desired product; mp 167°–170° C.; IR (KBr) 1775 cm$^{-1}$ (C=O); NMR (CDCL$_3$) δ1.38 (s, 9H, (CH$_3$)$_3$C), 2.85 (dd, 1H, J=3 and 6 Hz, 4βH), 3.25 (t, 1H, J=6 and 6 Hz, 4αH), 4.70 (m, 1H, 3αH), 5.25 (d, 1H, NH), 7.40 (m, 10H, aromatic protons).

EXAMPLE 4 t-Butyl (S)-[1-[(diphenylmethylene)amino]-2-(S)-methyl-4-oxo-3-azetidinyl]-carbamate; (4b)

The procedure of Example 3 (Mitsunobo reaction) was followed using N-(t-butyloxycarbonyl)-L-threonine-2-(2-diphenylmethylene)hydrazide in place of N-(t-butyloxycarbonyl)-L-serine-2-(diphenylmethylene)-hydrazide to give a white crystalline product (68%); IR (KBr) 1780 cm$^{-1}$; NMR (CDCL$_3$) δ1.20 (d, 3H, CH$_3$—), 1.45 (s, 9H, (CH$_3$)$_3$C), 3.35 (m, 1H, 2βH), 4.20 (m, 1H, 3αH), 7.50 (m, 10H, aromatic protons).

EXAMPLE 5 t-Butyl (S)-1-amino-2-oxo-3-azetidinylcarbamate; (5a)

A 2.1 g amount of t-butyl(S)-[1-[(diphenylmethylene)amino]-2-oxo-3-azetidinyl]carbamate was dissolved in 100 ml of ethyl alcohol and 50 ml of ethyl acetate and 0.5 g of 10% palladium on carbon catalyst was added. The mixture was hydrogenated in a Parr apparatus at 30 psi for 24 hours. The mixture was then filtered through diatomaceous earth and evaporated to dryness in vacuo. The residue was crystallized from ethyl acetate to give 0.75 g of the product of the example, mp 165°–168° C.; IR (KBr), 1750 cm$^{-1}$; NMR (d$_6$ DMSO) δ1.45 (s, 9H, (CH$_3$)$_3$C), 3.25 (dd, 1H), 3.50 (t, 1H), 4.50 (m, 1H), 7.55 (d, 1H, NH).

EXAMPLE 6 t-Butyl-1-amino-2-(S)-methyl-4-oxo-3-(S)-azetidinylcarbamate; (5b)

The procedure of Example 5 was followed for this example using t-butyl(S)-[1-[(diphenylmethylene)amino]-2-(S)-methyl-4-oxo-3-azetidinyl]carbamate in place of t-butyl (s)-[1-[(diphenylmethylene)amino]-2-oxo-3-azetidinyl]carbamate to give the desired product in 72% yield: IR (KBr) 1750 cm$^{-1}$ (β-lactam C=O); NMR (CDCL$_3$) δ1.40 (d, 3H, CH$_3$), 1.50 (S, 9H, (CH$_3$)$_3$C), 3.40 (dd, 1H, 2βH), 5.35 (d, 1H, 3αH).

EXAMPLE 7

Benzyl (S)-3-[t-butyloxycarbonylamino]-2-oxo-1-azetidinyliminoacetate; (7a)

A solution of 2.33 g (11.57 mmol) of t-butyl (S)-1-amino-2-oxo-3-azetidinylcarbamate and 1.90 g (11.57 mmol) of benzyl glyoxylate in 250 ml of toluene was refluxed for one hour using a water separator. The solution was then evaporated to dryness in vacuo and the residue was dissolved in methylene chloride, filtered through hydrous magnesium silicate and again evaporated at reduced pressure. The resulting oil was triturated to a solid with ether which was collected by filtration and crystallized from acetone:hexane to give 2.12 g in 53% yield, mp 128°–130.5° C.; IR (KBr), 1780 cm$^{-1}$ ($\beta$-lactam C=O); NMR (CDCL$_3$) $\delta$1.45 (s, 9H), 3.50 (m, 1H), 3.80 (t, 1H), 5.25 (m, 1H), 5.30 (s, 2H), 7.38 (s, 5H).

EXAMPLE 8

Benzyl-[[4-(S)-methyl-3(S)-[(t-butyloxycarbonyl)amino]-2-oxo]imino]acetate; (7b)

A solution of 5.34 g (24.8 mmol) of t-butyl-1-amino-2(S)-methyl-4-oxo-3-(S)-azetidinylcarbamate and 4.07 g (24.8 mmol) of benzyl glyoxylate in 250 ml of toluene was treated as described in the procedure of Example 7 to provide 7.31 g of product. Recrystallization from acetone:hexane gave 6.60 g, (76% yield) of the desired product, mp 154.5°–158° C., IR (KBr) 1765 cm$^{-1}$ ($\beta$-lactam C=O); NMR (DCCL$_3$); $\delta$1.45 (s, 9H), 1.52 (d, 3H, J=8 Hz), 4.25 (m, 2H), 5.65 (s, 2H), 7.65 (s, 5H), 8.25 (s, 1H).

EXAMPLE 9

3-(t-Butyloxycarbonylamino)-2-oxo-1-azetidinyliminoacetic acid; (8a)

A solution of 1.0 g (2.88 mmol) of benzyl (S)-3-(t-butyloxycarbonylamino)-2-oxo-1-azetidinyliminoacetate in 20 ml of tetrahydrofuran was hydrogenated at atmospheric pressure for three hours in the presence of 200 mg of 5% palladium on carbon. The catalyst was removed by filtration and the solution was evaporated in vacuo to give a foam which was crystallized from ethyl acetate:hexane; to give 650 mg of the product of the example in 88% yield, mp 145°–147° C., IR (KBr); 1800 cm$^{-1}$ ($\beta$-lactam, —C=O); NMR (d$_6$DMSO); $\delta$1.35 (s, 9H, t-butyl), 3.50 (m, 1H), 3.85 (dd, J=3, and J=6, 1H). 4.62 (m, 1H), 7.20 (s, 1H), 7.65 (d, 1H).

EXAMPLE 10

4(S)-Methyl-[[3(S)-[[(t-butyloxycarbonyl]amino]-2-oxo-1-azetidinyl]imino]acetic acid; (8b)

A solution of 3.0 g (8.3 mmol) of benzyl[[4-(S)-methyl-3(S)-[(t-butyloxycarbonyl)amino]-2-oxo]imino]acetate and 500 mg of 5% palladium on carbon in 70 ml of tetrahydrofuran was hydrogenated at atmospheric pressure for 3 hours and worked up as described in Example 9 to afford a foam: yield 2.58 g; IR (KBr) 1780 cm$^{-1}$; NMR (CDCL$_3$) $\delta$1.45 (s, 9H, (CH$_3$)$_3$C), 1.62 (d, 3H, J=8 Hz, CH$_3$), 4.25 (m, 2H), 8.75 (s, 1H=CH).

EXAMPLE 11

(S)-[(3-Amino-2-oxo-1-azetidinyl)imino]acetic acid trifluoroacetate; (9a)

A solution of 2.72 g (10 mmol) of 3-(t-butyloxycarbonylamino)-2-oxo-1-azetidinyliminoacetic acid in 10 ml of trifluoroacetic acid was stored at room temperature for 16 hours, then was evaporated to dryness in vacuo. The resulting oil was triturated to a solid with ether to afford 3.18 g of the desired salt; IR (KBr) 1780 cm$^{-1}$ ($\beta$-lactam C=O); NMR (d$_6$DMSO) $\delta$3.4 (dd, 1H, J=2.5 and 5.5 Hz), 4.25 (1H, t, J=5.5 Hz), 4.65 (dd, 1H, J=2.5 and 5.5 Hz.), 7.26 (s, 1H), 8.0–9.2 (m, 3H).

EXAMPLE 12

[[(S)-3-Amino-4-oxo-2-(S)-methyl-1-azetidinyl]imino]acetic acid trifluoroacetate; (9b)

The procedure of Example 11 was followed using 4(S)-methyl-[[3(S)-[[(t-butyloxycarbonyl]amino]-2-oxo-1-azetidinyl]imino]acetic acid in place of 3-(t-butyloxycarbonylamino)-2-oxo-1-azetidinyliminoacetic acid to afford the product of the example, mp 172°–174° C. dec; IR (KBr) 1780 cm$^{-1}$; NMR (TFA) $\delta$1.80 (d, 3H, J=8 Hz), 4.65 (broad s, 1H, 3$\alpha$H), 4.80 (d, 1H, J=8 Hz, 4H).

EXAMPLE 13

(S)-3-[2-(2-Amino-4-thiazolyl)]-(Z)-2-methoxyiminoacetylamino-2-(S)-methyl-4-oxo-1-azetidinyliminoacetic acid; (12b)

A mixture of 687 mg (3.42 mmol) of 2-(2-amino-4-thiazolyl-(Z)-2-methoxyiminoacetic acid, 705 mg (3.42 mmol) of dicyclohexylcarbodiimide and 523 mg (3.42 mmol) of 1-hydroxybenzotriazole in 18 ml of N,N-dimethylformamide was stirred at room temperature for 20 minutes. To this mixture was added a mixture of 830 mg (3.42 mmol) of [[(S)-3-amino-4-oxo-2-(S)-methyl-1-azetidinyl]imino]acetic acid trifluoroacetate, 1.30 ml (7.70 mmol) of chlorotrimethylsilane and 1.07 ml (7.70 mmol) of triethylamine in 15 ml of N,N-dimethylformamide. The resulting mixture was stirred at room temperature for 16 hours and then was filtered. The filtrate was diluted with 100 ml of water and extracted with two 50 ml portions of ethyl acetate. The aqueous phase was stirred for several hours with 50 ml of granular carbon. The liquid was decanted and the carbon was washed several times with water, then stirred for several hours with 50% v/v aqueous acetone (pH 3). The mixture was filtered and the filtrate was evaporated to dryness in vacuo. The residue was dissolved in a small amount of dimethyl sulfoxide and precipitated by the addition of ether to give the desired product; IR (KBr) 1775 cm$^{-1}$ ($\beta$-lactam C=O); NMR (d$_6$DMSO+TFA) $\delta$1.50 (d, 3H), 4.05 (s, 3H), 4.35 (m, 1H), 4.65 (d, 1H), 7.18 (s, 1H), 7.50 (s, 1H).

EXAMPLE 14

Allyl(S)-3-[t-Butyloxycarbonylamino]-2-oxo-1-azetidinyliminoacetate (14a)

A solution of 3.74 g (18.6 mmol) of S-3-[t-butyloxycarbonylamino]-2-oxo-1-aminoazetidine and 2.38 g (18.6 mmol) of allyl glyoxylate in 125 ml of toluene was heated at reflux for one hour using a water separator. The solution was then evaporated to dryness in vacuo. The residue was dissolved in dichloromethane and filtered through hydrous magnesium silicate. The filtrate was evaporated in vacuo to give 3.30 g (60%) of the desired product as a yellow glass; M+(FAB)297; IR(-mull)1795 cm$^{-1}$ ($\beta$-lactam C=O), 1720 cm$^{-1}$ (ester C=O); NMR (CDCl$_3$) $\delta$1.45 (s, 9H, (CH$_3$)$_3$C), 3.77 (dd, 1H, J=3.1, and 6.8 Hz, H$_4$ $\beta$), 4.02 (dd, 1H, J=6.8 and 6.4 Hz, H$_{4\alpha}$), 4.77 (d, 2H, J=5; 9 Hz, O CH$_2$), 4.80 (m, 1H, H$_{3\alpha}$), 5.20 (d, 1H, NH), 5.30 (d, 1H, J=10 Hz, allyl cis H), 5.38 (d, 1H, J=15.8 Hz, allyl trans H), 5.96 (m, 1H, CH2CH=), 7.44 (s, 1H, N=CH).

EXAMPLE 15

Allyl (S)-[(3-Amino-2-oxo-1-azetidinyl)imino]acetate trifluoroacetate (15a)

A solution of 2.97 g (9.76 mmol) of allyl (S)-3-[t-butyloxycarbonylamino]-2-oxo-1-azetidinyliminoacetate in 40 ml of trifluoroacetic acid was stored at room temperature for 1.0 hour. Then the solution was evaporated to dryness in vacuo at 35° C. The resulting oil was triturated to a solid with diethyl ether to afford 2.01 g (67%) of the desired salt; IR(KBr) 1775 cm$^{-1}$ ($\beta$-lactam C=O); NMR (DMSO) d 3.72 (dd, 1H, J=3.1 and 6.8 Hz, H$_{4\beta}$), 4.07 (dd, 1H, J=6.8 and 6.0 Hz, H4$\alpha$), 4.66 (dd, 1H, J=2.8 and 6.0 Hz), 4.75 (d, 2H, J=5.5 Hz, —OCH$_2$—), 5.28 (d, 1H, J=10 Hz, allyl cis H), 5.37 (d, 1H, J=16.8 Hz, allyl trans H), 5.98 (m, 1H, CH$_2$CH=), 7.40 (s, 1H, N=CH), 8.90 (broad s, 3H, +NH$_3$).

EXAMPLE 16

Allyl (S)-3-[(2-amino-4-thiazolyl)-(Z)-2-methoxyiminoacetylamino]-2-oxo-1-azetidinyliminoacetate (16)

A mixture of 2.0 g (10.0 mmol) of 2-(2-amino-4-thiazolyl)-(Z)-2-methoxyiminoacetic acid, 2.06 g (10.0 mmol) of dicyclohexylcarbodiimide and 1.53 g, (10.0 mmol) of 1-hydroxybenzotriazole in 50 ml of N,N-dimethylformamide was stirred at room temperature for 20 minutes. To this mixture was added a mixture of 3.12 g (10.0 mmol) of allyl (S)-[(3-amino-2-oxo-1-azetidinyl)imino]acetate trifluoroacetate and 2.08 ml (15.0 mmol) of triethylamine in 25 ml of N,N-dimethylformamide. The resulting mixture was stirred at room temperature for 16 hours and then was filtered. The filtrate was evaporated in vacuo at 40° C. to remove the N,N-dimethylformamide and the residue was chromatographed on silica gel using ethyl acetate as the eluent to afford 1.56 g (41%) of product: IR (KBr) 1777 cm$^{-1}$ ($\beta$-lactam C=O), 1719 cm$^{-1}$ (ester C=O). NMR (DMSO) $\delta$3.68 (dd, 1H, J=3.1 and 6.8 Hz, H$_{4\beta}$), 3.85 (s, 3H, CH$_3$), 4.06 (dd, 1H, J=6.8 and 6.4 Hz, H4$\alpha$), 4.74 (d, 2H, J=5.5 Hz, OCH$_2$). 5/01 (m, 1H, H$_3\alpha$), 5.28 (d, 1H, J=10 Hz, allyl cis H), 5.38 (d, 1H, J=16.2, allyl trans H), 5.98 (m, 1H, CHCH=), 6.74 (S, 1H, thiazole H), 7.24 (s, 2H, NH$_2$), 7.28 (s, 1H, N=CH), 9.31 (S, 1H, NH).

EXAMPLE 17

Potassium S-[[3-[[(2-amino-4-thiazolyl)-(Z)-(methoxyimino)-acetyl]amino]-2-oxo-1-azetidinyl]imino]acetate (12a)

A mixture of 180 mg (0.47 mmol) of allyl (S)-3-[(2-amino-4-thiazolyl)-(Z)-2-methoxyiminoacetylamino]-2-oxo-1-azetidinyliminoacetate, 38 mg of tetrakis(triphenylphosphine)palladium (O), 27 mg of triphenylphosphine and 1.0 ml of 0.5M potassium 2-ethylhexanoate solution (in ethyl acetate) in 10 ml of dichloromethane and 5 ml of ethyl acetate was stirred at room temperature under nitrogen for 40 minutes. The reaction mixture was diluted with 20 ml of ether and the resulting solid was collected by filtration. The solid was dissolved in a small volume of water, treated with activated charcoal, filtered and lyophilized to give 38.0 mg of the product of the example: IR (KBr) 1764 cm$^{-1}$ ($\beta$-lactam C=O). NMR (DMSO) $\delta$3.84 (S, 3H, CH$_3$O), 3.85 (m, 2H, H$_{4\alpha}$ and H$_{4\beta}$), 4.92 (m, 1H, H$_{3\alpha}$), 6.75 (S, 1H, thiazole H), 7.00 (S, 1H, CH=N), 7.22 (S, 2H, NH$_2$), 9.22 (d, 1H, J=7.5 Hz, —NH).

We claim:

1. A compound selected from the group consisting of those of the formula:

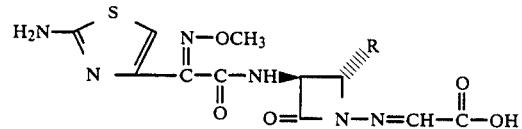

wherein R is hydrogen or methyl and the pharmacologically acceptable cationic salts thereof.

2. The compound according to claim 1; (S)-3-[2-(2-amino-4-thiazolyl)]-(Z)-2-methoxyiminoacetylamino-2-(S)-methyl-4-oxo-1-azetidinyliminoacetic acid.

3. The compound according to claim 1; (S)-3-[2-(2-amino-4-thiazolyl)]-(Z)-2-methoxyiminoacetylamino-2-oxo-1-azetidinyliminoacetic acid.

4. The method of treating bacterial infections in a mammal which comprises administering to said mammal a pharmacologically effective amount of a compound of claim 1.

5. A composition of matter in dosage unit form for the treatment of bacterial infections in mammals comprising from about 25 mg to about 250 mg per dosage unit of a compound of claim 1 in association with a pharmaceutically acceptable carrier.

* * * * *